United States Patent [19]
Thust et al.

[11] Patent Number: 5,632,381
[45] Date of Patent: May 27, 1997

[54] APPARATUS FOR SORTING MATERIALS

[75] Inventors: Walter Thust, Achim; Jurgen Kirchhoff, Stuhr; Hans-Dieter Held; Leo Uelhoff, both of Bremen, all of Germany

[73] Assignee: DST Deutsch System-Technik GmbH, Bremen, Germany

[21] Appl. No.: 441,231

[22] Filed: May 15, 1995

[30] Foreign Application Priority Data

May 17, 1994 [DE] Germany ............................ 44 17 257.5

[51] Int. Cl.[6] ............................................... B07C 5/00
[52] U.S. Cl. ......................... 209/44.1; 209/590; 209/692
[58] Field of Search ................................. 209/12.1, 44.1, 209/577, 579, 580, 587, 590, 692, 693, 930, 939, 920

[56] References Cited

U.S. PATENT DOCUMENTS

| | | | |
|---|---|---|---|
| 2,635,746 | 4/1953 | Gordon | 209/590 X |
| 3,975,261 | 8/1976 | Beck | 209/590 X |
| 5,423,431 | 6/1995 | Westin | 209/930 X |

*Primary Examiner*—David H. Bollinger
*Attorney, Agent, or Firm*—Merchant, Gould, Smith, Edell, Welter & Schmidt, P.A.

[57] ABSTRACT

An apparatus for sorting paper materials includes a separating mechanism for thinning the paper materials and a sensing mechanism for classifying the paper material according to type. The separating mechanism includes a plurality conveyor belts operating at successively higher speeds, whereby passing materials from one conveyor belt to another conveyor belt results in spreading the paper material. The sensing mechanism includes a mechanical striking device to strike the paper material, a microphone to detect the sound caused by the striking device and an evaluation unit to determine the type of paper material on the basis of the sound.

39 Claims, 3 Drawing Sheets

5,632,381

APPARATUS FOR SORTING MATERIALS

FIELD OF THE INVENTION

This invention relates to an apparatus for sorting materials.

DESCRIPTION OF RELATED ART

For instance, a sorting apparatus is known that comprises a steeply upward-directed, perforated conveyor belt and a suction device underneath the conveyor belt that draws the materials against the belt strand, which runs in the direction of conveyance.

This familiar sorting apparatus is suitable for separating plastic films and other plastic materials. The plastic films are drawn, by the suction device, against the belt strand that runs in the direction of conveyance, while the rest of the plastic material slides off the conveyor belt because the contact surface with the conveyor belt is too small compared to their weight. However, this familiar sorting mechanism is unsuitable for sorting paper and cardboard.

Another generally known apparatus for sorting waste paper comprises an ascending conveyor that transports waste paper, which is loaded in batches into an underground shaft by a bucket loader, on a conveyor belt. On the conveyor belt, the material is sorted manually according to paper or cardboard type. Depending on the day order, specific kinds of materials such as newspapers, illustrated papers, etc. are removed from the stream of waste paper and tossed in corresponding dropping shafts or containers.

The drawback of this familiar sorting apparatus consists especially in the low degree of automation and the high labor costs connected to it.

SUMMARY OF THE INVENTION

It is the task of the invention to create an apparatus of the type mentioned in the beginning that can also sort paper and cardboard according to specifiable types of material. This problem is solved according to the invention in an apparatus of the type mentioned in the beginning by a mechanism for separating the material, and a sensing device behind the separating mechanism for classifying the material according to the condition of the material.

The advantages of the invention lie especially in that the apparatus according to the invention is suitable for automatic sorting of cardboard and paper. The separating mechanism thins out the material, which is first supplied in a continuous stream, so that individual objects overlap only insignificantly. After the thinning out, a sensing device makes an automatic determination of the type of the conveyed materials that, for instance, makes possible the control of a discharge mechanism that loads different receptacles, depending on the type of material detected.

Depending on the order, certain types of material are specified to the sensing device that can be continuously detected and sorted out. The operating costs of that kind of apparatus are relatively low because no personnel are needed for the sorting.

The separating mechanism advantageously comprises a first perforated conveyor belt and, immediately following, a second perforated conveyor belt that runs with a higher speed than the first conveyor belt, to stretch out the stream of materials to separate them.

Under the upper strand of each conveyor belt is provided, in each case, a suction chamber that ensures sufficient adhesion between the material and the conveyor belt by drawing air through the perforations of the conveyor belt. At the very high conveying speeds necessary for the separation, the suction chambers guarantee that the material on the conveyor belt—in particular, paper—does not slide off or whirl up.

The upper strand of the first conveyor belt advantageously has a predetermined upward-directed slope. Hereby especially heavy components of the stream of material can already be sorted out at the beginning of the conveyor track, such as, e.g., telephone books, catalogs, etc., whose weight is so great that they slide off the first conveyor and can be collected under it or supplied to another conveyor.

In a preferred embodiment of the invention, the slope of the upper strand of the second conveyor is smaller than that of the upper strand of the first conveyor. Advantageously, a supply belt is provided that supplies the materials to the first conveyor.

Between the discharge end of the additional conveyor and the first conveyor there remains a predetermined gap through which the material sliding down the first conveyor belt can drop down and either be collected there or transported away on another conveyor. In this manner, sorting out heavy material—for instance, telephone books, catalogs, etc. during the sorting of waste paper—is possible behind the supply conveyor.

Advisedly, a vibrating device is arranged at the supply belt that causes a shaking motion, superimposed on the conveying motion of the supply belt, to guarantee an even distribution of the material on the upper strand of the supply belt.

An especially preferred embodiment of the invention comprises a sensing device with a mechanical strike mechanism that strikes against the material at specifiable intervals, at least one acoustical receiver that detects the sound produced by the striking device when it strikes, and an evaluation unit connected to the receiver that determines the respective type of material from the detected sound.

The advantages of this embodiment lie especially in that, when being struck, paper and cardboard produce acoustical signals that make possible an accurate classification of the material. The evaluation of the sensor signals takes place in real time so it can simultaneously control a removal mechanism connected after it.

An embodiment of the mechanical striking mechanism comprises a ram that strikes against the material at specifiable time intervals. An alternative preferred embodiment of the mechanical striking mechanism comprises a rotatable and drivable wheel on whose circumferential surface one or more projections have been arranged. The wheel can be arranged at a conveyor belt of a sorting device in such a manner that the projections on the circumferential surface of the wheel strike against the material being transported.

The time intervals between two strikes can be determined in a simple manner by controlling the speed of the wheel. To obtain a uniform striking frequency at constant speed of the wheel, the projections should be evenly spaced on the circumferential surface of the wheel.

Advisedly, the receiver comprises two microphones and the evaluation comprises an electronic differential amplifier. The evaluation unit analyzes the differential signal produced by the differential amplifier as a time signal. In addition to, or alternatively to this, a Fourier transformation of the differential signal can be carried out and the frequency spectrum produced in this manner can be analyzed. The evaluation unit compares the time signal, or the frequency spectrum, with empirically determined reference data and determines the type of the material from the conformity of the time signal or the frequency spectrum with the reference data.

It is especially preferred if the sensing device comprises, in addition, a color sensor and a photo-evaluation unit connected to the color sensor that transmits the color information of the material to the evaluation unit.

To suppress undesired portions of the light reflected on the material, it is advisable to provide an infra-red filter between the color sensor and the material.

The color sensor advantageously consists of a commercial video camera that, compared to a simple color-recognizing sensor, has the advantage that all color information on the surface of the material can be detected. The photo-evaluation unit breaks down the video fields produced by the video camera in real time in individual windows and determines the average values of the color portions for each individual window. The average values can subsequently be integrated and transmitted to the evaluation unit as additional classification parameters.

Advisedly, the sensing device comprises an illuminating mechanism—in particular, a halogen lighting device to illuminate the material that is to be classified. With the illuminating device, a desired intensity of the light reflected on the material is produced.

It is especially preferred if, in addition, the sensing device comprises a mechanism for detecting the gloss properties of the material. This mechanism is formed by an illuminating device, preferably an infrared illuminating device, and a brightness sensor that measures the light emitted by the illuminating device and reflected on the material, as well as a device for detecting the gloss value, connected to the brightness sensor, that determines the gloss properties of the material from the brightness values measured by the brightness sensor and transmits them to the evaluation device.

Advisedly, the brightness sensor and the illuminating device are arranged in such a manner that the connecting line between the illuminating device and the material encloses the same angle with the horizontal as the connecting line between the brightness sensor and the material, whereas the brightness sensor, the illuminating device, and the material being transported lie in one plane. The advantages of the device for determining the gloss properties for the material lie in that another classification parameter is available for the evaluation device.

The brightness sensor can be formed by a video camera—in particular, by a black-and-white camera. For reasons of costs it would also be conceivable to use a video camera simultaneously as a color sensor and a brightness sensor.

Advisedly, the sensing device comprises an indicating device, connected to the evaluation unit, that indicates the classification result. By the indicating device, the function of the sensing device can be continuously examined, and it can be established to what type the material being presently transported belongs.

An especially preferred embodiment of the invention provides that the separating mechanism comprises a third conveyor that adjoins the second conveyor. The third conveyor belt runs with a higher speed than the second conveyor belt. The stream of material is further stretched by the third conveyor to attain improved spread.

The output of the suction chambers of each pair of conveyor belts is different in each case. Depending on the transported material, the speed and the slope of the upper strand of the respective conveyor belt, and the perforation of the conveyor belt, the output of the suction chambers is controlled or regulated in such a manner that a desired static friction is realized between the transported material and the conveyor belt.

At the end of the conveyor track of at least one conveyor belt, a blower is provided that generates an air current directed through the perforations of the conveyor belt to the transportation surface of the conveyor belt to guarantee a reliable transfer of the material to the conveyor belt which, in each case, is arranged after it.

To clean the conveyor belts, a rotating brush—which keeps especially the perforations of the conveyor belt open—runs against each conveyor belt.

The air current produced on a conveyor belt, in each case, by a suction chamber is preferably directed basically vertically in a central section of the upper strand and obliquely to the transportation surface at the discharge end of the conveyor to guarantee a reliable transfer of the material from one conveyor to the conveyor which, in each case, is arranged after it.

A preferred embodiment of the sorting mechanism comprises at least a conveyor belt that has openings through which the mechanical striking device strikes against the transported material from below. The distance between two openings is attuned to the striking frequency of the mechanical striking device and the speed of conveyance of the conveyor belt. Advisedly, the drives of the conveyor belt and the mechanical striking device are synchronized to ensure that the mechanical striking device strikes in the direction of the conveyor belt only when an opening passes over the striking device.

Alternatively, the sorting device has two synchronously running conveyor belts that are staggered parallel to each other at a small lateral distance. The mechanical striking device strikes from below—between the conveyor belts—against the material being transported. The advantage of this embodiment lies especially in that no synchronization is necessary between the mechanical striking device and the conveyor belts. The strike frequency can be regulated independently of the speed of conveyance.

Another preferred embodiment of the sorting device according to the invention provides that the mechanical striking device comprises a drivable wheel on whose circumferential surface at least one projection has been arranged. The wheel is located in such a manner that the projections of the wheel strike against the material.

To determine when an object reaches and exits the measuring range of a conveyor track, it is advisable that the sensing device comprises a light barrier with a light emitter and a light receiver and that the light emitter and light receiver are located above the conveyor track.

The light emitter and the light receiver are directed to the conveyor track and determine the time of entry and exit of an object in the measuring range on the basis of different reflective properties of the conveyor belt, on the one hand, and of the transported material, on the other hand.

An especially preferred embodiment of the invention provides that the conveyor track of the sorting device comprises at least one curved measuring segment that, in a cross-section, is trough-shaped; that the sensing device comprises, above the measuring segment, a distance sensor that determines the distance between the distance sensor and the material; and that the evaluation unit determines the stiffness of the material from the measured distances.

The advantages of this embodiment lie especially in that the elasticity properties of the material—which, in sorting devices with level conveyor tracks, can be detected only with difficulty by sensor technology—can be detected in a simple manner with common distance sensors. Flexible material such as, e.g., a picture magazine, adapts to the trough-shaped curved measuring section.

The distance sensor will detect this property by detecting a basically non-constant distance to the material. On the contrary, with stiff material such as, e.g., cardboard, the distance sensor will detect more or less constant distances from the material, depending on the shape of the measurement section.

The distance sensor comprises, e.g., a laser that directs a laser beam on the material on the conveyor track, and an optical sensor that detects the light signals reflected on the material on the conveyor track. If the laser beam encloses a small angle with the vertical, the spot radiated by the laser beam on the material shifts to the side according to the distance to the laser. This shifting of the light point can be detected in a simple manner with image-evaluation methods. The optical sensor is expediently developed by a commercial video camera. The distance sensor determines the distance to the material on the conveyor track either continuously over time or in specifiable time intervals.

Alternatively, the sagging of the material can be determined by a so-called light-slit method. For this purpose, a laser light line is projected—for instance, by a laser scanner—transverse to the trough, under a certain angle of inclination, onto the material in the measurement section. The line, which is more or less strongly curved, depending on the sagging of the material, is measured by a commercial video camera and evaluated by an image-evaluating device arranged after it.

At the end of the conveyor track, the sorting apparatus advisedly contains a discharge device that loads different receptacles, depending on the detected types of material. By coupling the discharge mechanism to the sensor, fully automatic sorting of the material is attained without the need for additional manual labor.

The arrangement of the perforations in the conveyor belts advantageously supports the thinning-out of the stream of material. For this purpose, perforated and unperforated sections are alternately provided in the conveyor belts of the separation mechanism. Between each of two perforated sections—which can correspond in their size to, e.g., that of a DIN-A4 sheet—an unperforated section is provided in which no paper is attracted by suction to additionally support the thinning-out of the stream of material.

The sorting apparatus is used with a special preference for classifying and sorting paper and cardboard. Advantageous further developments of the invention are characterized by the features of the subclaims.

BRIEF DESCRIPTION OF THE DRAWINGS

In the following, an embodiment of the invention is illustrated with the use of the enclosed drawings. Shown are.

DETAILED DESCRIPTION OF THE ILLUSTRATED EMBODIMENTS

Figure 1:
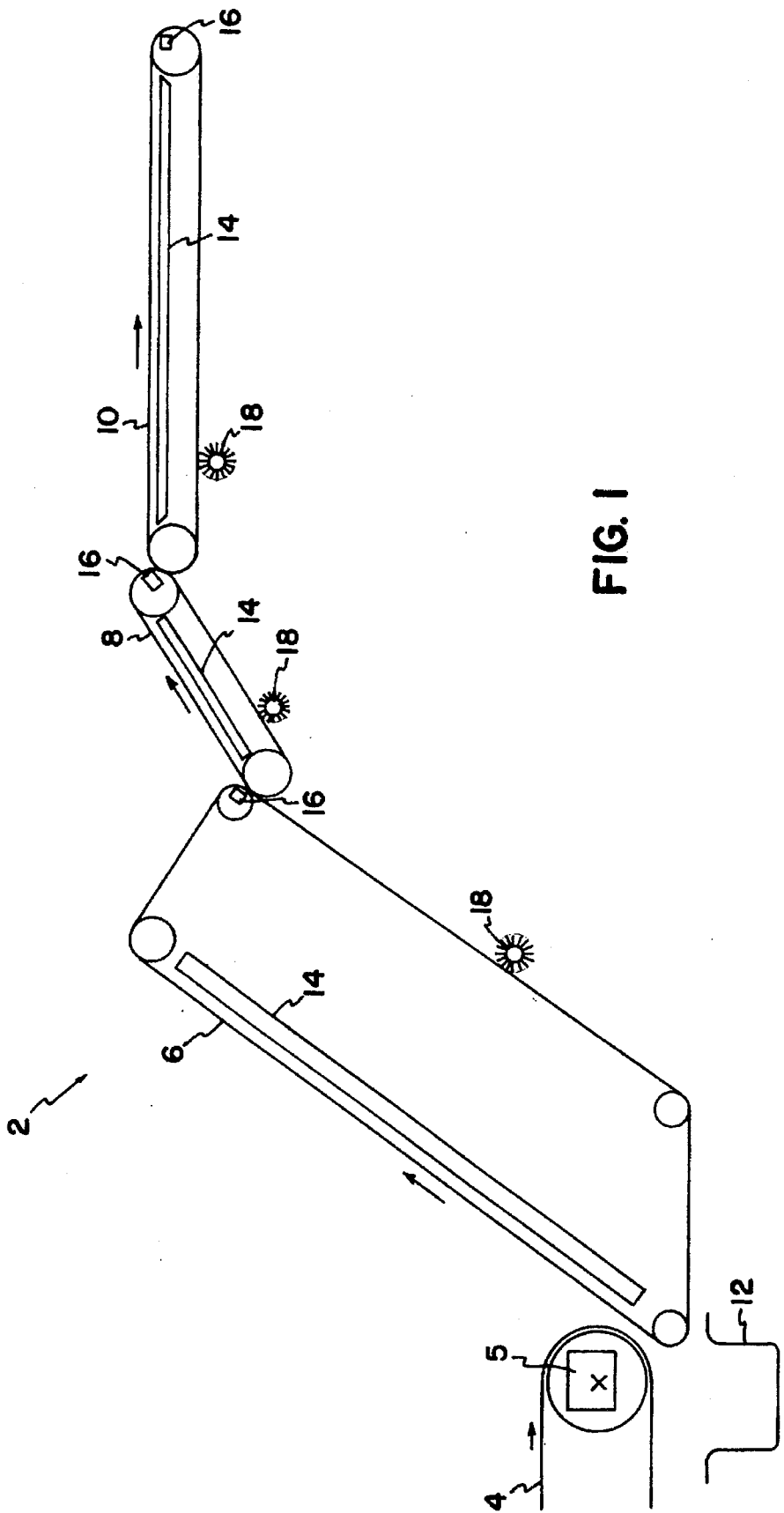
FIG. 1 is an isolation mechanism of a sorting device for isolating a stream of material consisting of paper and cardboard.

FIG. 1 shows a separating mechanism (2) of an apparatus for sorting paper and cardboard. The separating mechanism (2) has a supply belt (4) and a first, second, and third conveyor (6, 8, and 10) following one another. The direction of conveyance of the supply belt (4) and of the conveyor belts (6, 8, and 10) is indicated, in each case, with an arrow.

During the operation of the sorting device, the material is loaded onto the supply belt (4) with a bucket loader. A vibrating device (5) produces a shaking motion of the supply belt (4), superimposed on the motion of conveyance, to evenly distribute the material being transported on the supply belt.

The discharge end of the supply belt (4) is located at a predetermined distance from the first conveyor belt (6). Hereby a gap emerges between the supply belt (4) and the first conveyor belt (5), through which material sliding down the first conveyor belt (6) can slide downward and fall into a collecting chute (12) there.

The upper strand of the first conveyor belt (6) (the so-called ascending belt) is directed steeply upward in a longer section and is directed downward in a subsequent section that extends up to the discharge end. The slope of the upper strand of the adjoining second conveyor belt (8) is smaller than that of the first section of the first conveyor belt (6).

The second conveyor belt (8) runs with a higher speed of conveyance than the first conveyor belt (6). The second conveyor belt (8) is immediately followed by the third conveyor belt (10) whose upper strand runs basically horizontally. The speed of conveyance of the third conveyor belt (10) is higher than that of the second conveyor belt (8).

The first, second, and third conveyor belts (6, 8, and 10) are pierced with holes, or perforated. The piercing, or perforation, basically extends over the entire surface of conveyor belts (6, 8, and 10) respectively. Underneath the conveyor belts (6, 8, and 10) is located, in each case, a suction chamber (14) that draws in air through the perforations in the conveyor belts (6, 8, 10) respectively.

At the discharge end of the first, the second, and the third conveyor belts (6, 8, and 10) is provided, in each case, a blower (16) that generates an air current, which is directed to the transportation surface of the respective conveyor belts (6, 8, and 10). A rotating brush (18), which removes dirt from the conveyor belts (6, 8, and 10) and, in particular, from the perforations in the conveyor belts (6, 8, and 10) with its brush hairs, is installed at each conveyor belt (6, 8, and 10).

Figure 2:
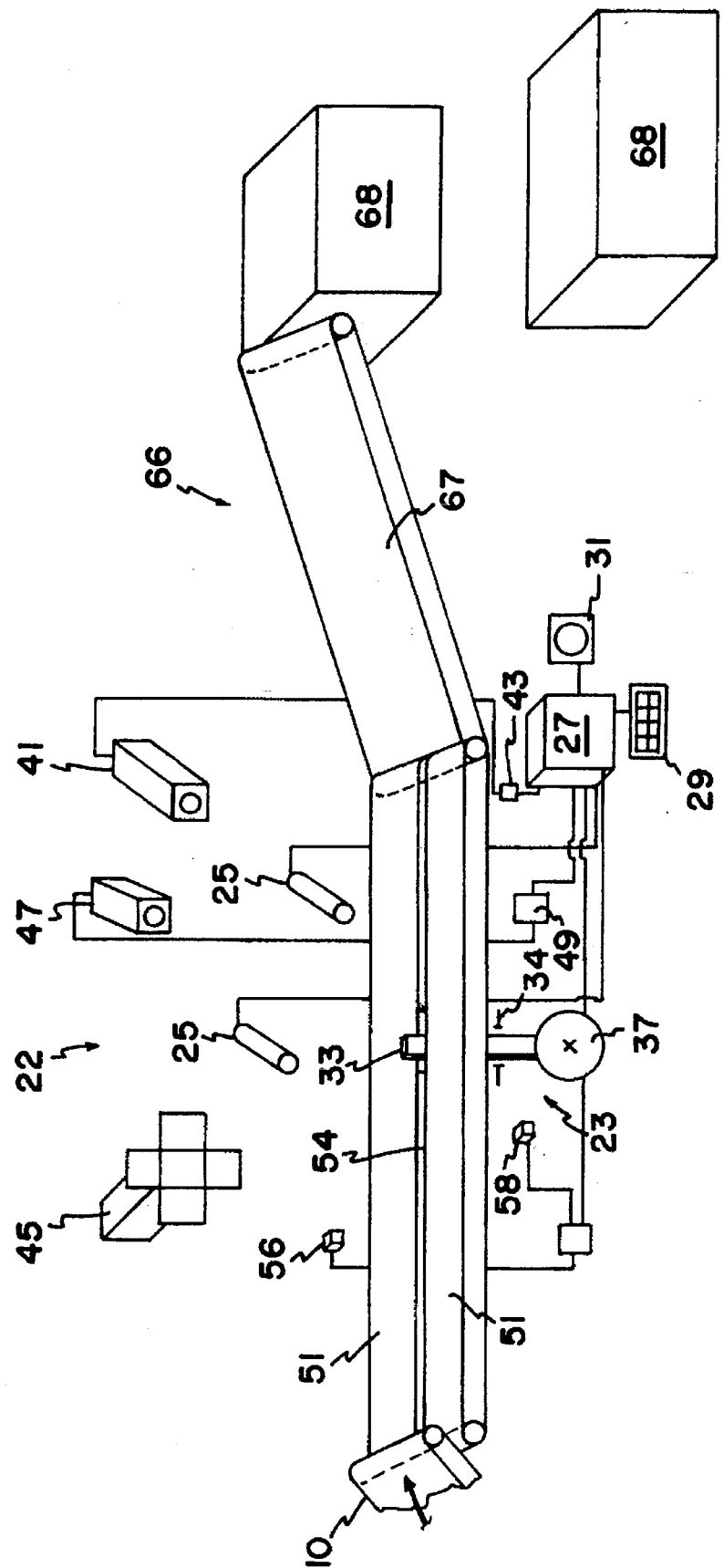
FIG. 2 is a sensor, located downstream of the separating mechanism represented in FIG. 1, for classifying the material.

A sensing mechanism (22) represented in FIG. 2 is located behind the separating mechanism (2). The sorting apparatus comprises two basically horizontally running conveyor belts (51)—which adjoin the third perforated conveyor belt (10), represented partially in FIG. 2—that run parallel to each other, staggered at a slight lateral distance, and enclose a slit-like gap (54). A discharge mechanism (66) for loading containers (68) adjoins at the end of the upper strand of the conveyor belts (51).

Underneath the conveyor belt (51) is arranged a motor-driven wheel (37) to which is hinged arm (33), eccentric to the axis of rotation. The rotary motion of the wheel (37) is transferred into an up-and-down motion of the ram (33) by a guide (34). However, the ram (33) is located in such a manner that, in its upper position, it reaches through the gap (54) between the conveyor belts (51) and, in its lower position, is located underneath the conveyor plane.

The temporal intervals in which the ram (33) moves upward between the conveyor belts (51) can be predetermined by controlling the speed of rotation of the wheel (37).

Two microphones that detect the sound produced when the ram (33) strikes against the material are arranged above or below the conveyor belts (51), at a distance from each other. The microphones (25) are connected, by way of a signal-processing circuit, with an evaluation unit (27) that classifies the material, on the basis of the detected sounds, by means of a differential amplifier that is not represented in more detail. A keyboard (29) and a display unit (31) are connected to the evaluation unit (27).

A video camera (41), arranged above the conveyor belts (51) and directed to the conveyor track, is provided for the evaluation of color information. The video camera (41) is connected to an image-evaluating unit (43) that determines color information about the material on the basis of the output signal of the video camera (41). The image-evaluating unit (43) is connected to the evaluation unit (27) to make possible a data exchange.

A brightness sensor, which is also developed as a video camera, is located above the upper strand of the conveyor belts (53) and directed toward the conveyor track. The brightness sensor (47) measures the light emitted by an illuminating device (45) and reflected by the material, and transmits the video fields to a gloss-evaluating device (49) that is connected to an evaluation unit (27).

Above the conveyor plane are located a light emitter (56) and a light receiver (58) at the opposite end of the conveyor track. The light emitter (56) sends light signals in the direction of the material being transported that, when reflected by the material, are received by the light receiver (58). The reflection of the light by the (for instance, black) conveyor belt is negligible so that it can be determined whether material is located in the measuring section. The light receiver (58) is connected to the evaluation unit (27) that, on the basis of the measure values, determines when an individual object enters the measuring range and when it leaves again.

Figure 3:
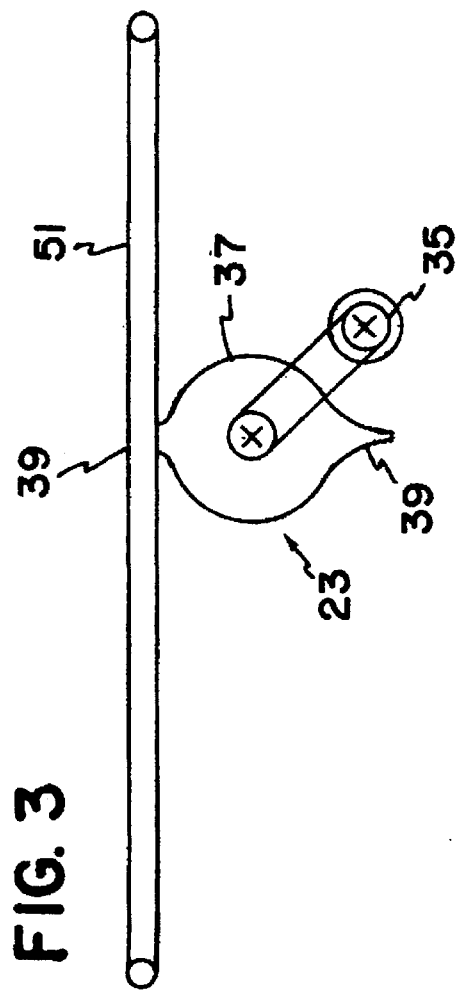
FIG. 3 is a mechanical striking device.

FIG. 3 shows a lateral view of the conveyor belts (51) and a second embodiment of the mechanical striking mechanism (23).

The mechanical striking mechanism (23) comprises a wheel (37), driven by means of a motor (35), on whose circumferential surface two projections (39) are located, opposite each other.

In the represented arrangement of the wheel (37) with respect to the conveyor belt (51), the projections (39) at the upper reversal point of their track of travel reach, each time, through the gap (54) between the conveyor belts (51) and can strike against the material.

The circumferential surface of the wheel (37) is located underneath the conveying plane of the conveyor belts (51).

Figure 4:
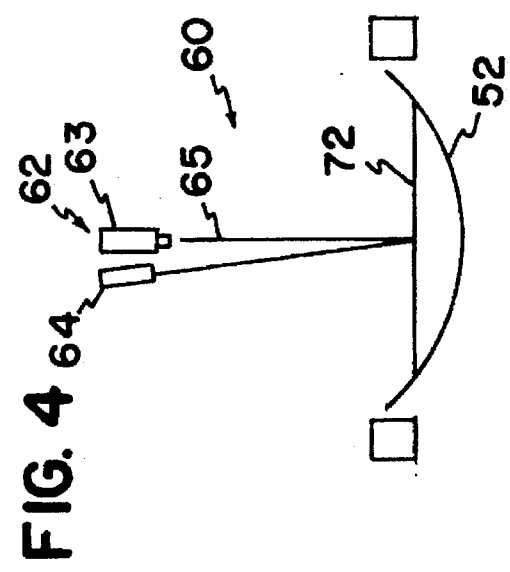
FIG. 4 is a cross-section transverse to the direction of conveyance of the upper strand of a conveyor belt of a sorting device, and a mechanism for determining the stiffness of the material.

FIG. 4 shows the upper strand of a conveyor section of a sorting device with a conveyor belt (52) that, in a cross-section, comprises a trough-shaped measuring section (60).

Above the measuring section (60) is arranged a distance sensor (62) that comprises a laser (63) whose beam (65) is directed to the measuring segment (60), with a predetermined angle to the vertical, and an optical sensor (64) that measures the light signals reflected by the material (72) on the conveyor track. The distance sensor (62) is connected to the evaluation unit (27) that determines information about the stiffness of the material (72) on the basis of the measured values.

On the conveyor belt (52) is material (72) consisting of cardboard that, because of its stiffness, does not lie on the conveyor belt (52) in the measuring section (60) with its entire surface but is propped up with its lateral edges against the conveyor belt (52) on the side. The laser beam (65) directed onto the material (72) by the laser (63)—developed, in the present embodiment, as a laser scanner—is reflected by the material (72) and produces, on the material (72), a light line that is detected by the optical sensor (64).

Because of the fact that the laser beam (65) encloses a predetermined angle to the vertical, the light line will be more or less curved, depending on the sagging of the material. Using this curvature of the line produced by the light points, it is determined whether the material is stiff and whether, in a stream of wastepaper, it therefore consists of cardboard.

Alternatively, the laser (33) can be developed as a simple laser that, without a scanning device, directs a light beam onto the measuring track under a predetermined angle to the vertical. In case of that kind of laser (63), the light point of the laser beam (65) shifts to the side, in the reflection plane, with increasing or decreasing distance of the material (72) from the conveyor belt (52). Using this lateral shifting of the light point, it can be determined in this embodiment whether the material sags or whether it is stiff.

In another embodiment of the invention, not represented in more detail, also conveyor belts (51 and 52) can be perforated and a suction chamber for drawing air through the perforations of the conveyor belt (51, 52) is arranged, in each case, under the upper strand of these conveyor belts (51, 52).

The described types of mechanical sensors can also be arranged on a sliding metal plate with a corresponding opening that is connected to the conveyor belt (10). Thereby, perforating or slitting the conveyor belt (51) is dispensed with.

We claim:

1. Apparatus for detecting material characteristics of material on a conveyor belt, comprising:

a separating mechanism for thinning out the material, the separating mechanism comprising a first perforated conveyor belt, an immediately following second perforated conveyor belt having a speed of conveyance larger than a first speed of conveyance of the first conveyor belt, and first and second suction chambers respectively under upper strands of the first and second conveyor belts to draw air in through perforations in respective conveyor belt; and a sensing mechanism following behind the separating mechanism to classify the material according to the condition of the material, the sensing mechanism comprising a mechanical striking device to strike against the material at predetermined time intervals, at least one acoustical receiver to detect noise produced by the striking device striking against the material, and an evaluation unit connected to the receiver to determine a type of material in response to detected noise.

2. Apparatus according to claim 1, wherein the upper strand of the first conveyor belt has a predetermined upward-directed slope.

3. Apparatus according to claim 2, wherein the upper strand of the second conveyor belt has a slope smaller than a slope of the upper strand of the first conveyor belt.

4. Apparatus according to claim 3, further comprising a supply belt to supply the material to the first conveyor belt, and having a discharge end positioned at a predetermined distance from the first conveyor belt.

5. Apparatus according to claim 4, further comprising a vibrating device in the supply belt to cause a shaking motion of the supply belt superimposed on the conveying motion.

6. Apparatus according to claim 1, wherein the sensing mechanism is adapted to determine the type of material in real time.

7. Apparatus according to claim 1, wherein the mechanical striking device comprises a ram to strike against the material.

8. Apparatus according to claim 1, wherein the mechanical striking device comprises a rotatable and drivable wheel having a circumferential surface, one or more projections being arranged on the circumferential surface.

9. Apparatus according to claim 1, wherein the acoustical receiver comprises two microphones, the evaluation unit comprises an electronic differential amplifier, and an output of each microphone lies at respective inputs to the differential amplifier.

10. Apparatus according to claim 9, wherein the evaluation unit analyzes a differential output signal produced by the differential amplifier as a time signal.

11. Apparatus according to claim 10, wherein the evaluation unit transforms the differential output signal produced by the differential amplifier into a Fourier series to produce a frequency spectrum and analyzes the frequency spectrum.

12. Apparatus according to claim 1, wherein the sensing mechanism further comprises a color sensor and an image-evaluation unit connected to the color sensor, the image-evaluation unit transmitting color information of the material to the evaluation unit.

13. Apparatus according to claim 12, wherein the color sensor comprises an infrared filter.

14. Apparatus according to claim 12, wherein the color sensor is a video camera and the image-evaluation unit is adapted to break down video fields into individual windows in real time and determine average values of color portions for each individual window.

15. Apparatus according to claim 1, characterized in that the sensing mechanism comprises an illuminating device to illuminate the material to be classified.

16. Apparatus according to claim 1, wherein the sensing mechanism comprises a detecting device for detecting gloss properties of the material, the detecting device including an illuminating device, a brightness sensor to measure light emitted by the illuminating device and reflected by the material, and a gloss-detecting device connected to the brightness sensor, to determine gloss properties of the material and transmit the gloss properties to the evaluation unit in response to brightness values measured by the brightness sensor.

17. Apparatus according to claim 16, wherein the illuminating device and a portion of material being analyzed form a first angle with a horizontal line, the brightness sensor and the portion of material form a second angle with the horizontal line equal to the first angle, and the brightness sensor, the illuminating device, and the portion of material lie in plane.

18. Apparatus according to claim 16, wherein the brightness sensor is a black-and-white video camera.

19. Apparatus according to claim 1, further comprising an indicating device connected to the evaluation unit to indicate a determination by the evaluation unit.

20. Apparatus according to claim 1, wherein the separating mechanism comprises a third perforated conveyor belt immediately following the second conveyor belt to receive material from the second conveyor belt.

21. Apparatus according to claim 20, wherein the third conveyor belt has a speed of conveyance higher than the speed of conveyance of the second conveyor belt.

22. Apparatus according to one of claim 21, wherein the third conveyor belt has an upper strand with a slope less than a slope of the upper strand of the second conveyor belt.

23. Apparatus according to claim 22, further comprising a third suction chamber below the upper strand of the third conveyor belt and wherein the first, second and third suction chambers have differing suction power.

24. Apparatus according to claim 23, further comprising a blower to generate an air current through perforations at a conveying end of one of the first, second and third conveyor belts, the air current being directed from an inner portion of the one of the first, second and third conveyor belts to a transportation surface of the one of the first, second and third conveyor belts.

25. Apparatus according to claim 23, wherein the first, second and third suction chambers each produce respective air currents directed essentially perpendicular to respective transportation surfaces at central portions of respective conveyor belts and directed essentially off perpendicular from the respective transportation surfaces of the respective conveyor belts at respective discharge ends of respective conveyor belts.

26. Apparatus according to claim 20, wherein one of the first second and third conveyor belts is provided with a rotating brush to clean the one of the first, second and third conveyor belts.

27. Apparatus according to claim 20, wherein one of the first, second and third conveyor belts has openings and the mechanical striking device strikes the material through the openings from below the upper strand of the one of the first, second and third conveyor belts.

28. Apparatus according to claim 27, wherein the one of the first, second and third conveyor belts comprises two synchronously running conveyor belts arranged in parallel, and staggered at a small lateral distance, and the mechanical striking device strikes the material from below, between the two synchronously running conveyor belts.

29. Apparatus according to claim 28, wherein the sensing mechanism comprises a sliding metal plate with a window-like opening between the two synchronously running conveyor belts, and the mechanical striking device strikes against the material through the window-like opening.

30. Apparatus according to claim 20, wherein one of the first, second and third conveyor belts comprises a measuring section having a trough-shaped cross-section, the sensing mechanism comprises, a distance sensor positioned above the measuring section to determine distance between the distance sensor and the material, and the evaluation unit determines stiffness of the material on the basis of measured distances.

31. Apparatus according to claim 30, wherein the distance sensor comprises a laser and an optical sensor.

32. Apparatus according to claim 30, wherein the distance sensor comprises a laser scanner and an optical sensor.

33. Apparatus according to claim 30, wherein the distance sensor comprises a video camera.

34. Apparatus according to claim 20, wherein the first, second and third conveyor belts are evenly perforated.

35. Apparatus according to claim 20, wherein the first, second and third conveyor belts each respectively comprise perforated and nonperforated sections.

36. Apparatus according to claim 1, wherein the mechanical striking device comprises a drivable wheel having a circumferential surface and at least one projection arranged on the circumferential surface so as to strike against the material when the drivable wheel is rotated.

37. Apparatus according to claim 1, wherein the sensing mechanism comprises a light barrier with a light emitter and a light receiver arranged above one of the first and second conveyor belts.

38. Apparatus for detecting material characteristics of paper or cardboard material transported by a conveyor belt, comprising:

a separating mechanism for thinning out the material on the conveyor belt; and a sensing mechanism following the separating mechanism to classify the material according to the condition of the material, the sensing mechanism comprising a mechanical striking device to strike against the material in specifiable time intervals, at least one acoustical receiver to detect noise produced by the striking device upon striking the material, and an evaluation unit connected to the receiver to determine a respective material type in response to the detected noise.

39. A method of classifying paper and cardboard material, comprising the steps of:

passing the material from a first conveyor belt operating at a first speed to a second conveyor belt operating at a second speed higher than the first speed so as to separate the material;

mechanically striking the material at predetermined intervals;

detecting noise produced by the striking step; and determining a material type in response to the noise detected.

* * * * *